US008859481B2

(12) United States Patent
Clark et al.

(10) Patent No.: US 8,859,481 B2
(45) Date of Patent: Oct. 14, 2014

(54) WIPER FOR USE WITH DISINFECTANTS

(75) Inventors: James William Clark, West Chester, PA (US); Philip Shi Hung Hui, Alpharetta, GA (US); James J. Detamore, Atlanta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 869 days.

(21) Appl. No.: 11/300,751

(22) Filed: Dec. 15, 2005

(65) Prior Publication Data

US 2007/0142261 A1   Jun. 21, 2007

(51) Int. Cl.
| | |
|---|---|
| *C11D 17/00* | (2006.01) |
| *C11D 17/08* | (2006.01) |
| *C11D 3/02* | (2006.01) |
| *C11D 3/00* | (2006.01) |
| *C11D 1/62* | (2006.01) |
| *A01N 25/34* | (2006.01) |
| *C11D 17/04* | (2006.01) |
| *A61K 8/02* | (2006.01) |
| *A61Q 17/00* | (2006.01) |

(52) U.S. Cl.
CPC ............. *C11D 17/049* (2013.01); *C11D 1/62* (2013.01); *A01N 25/34* (2013.01); *A61K 8/0208* (2013.01); *A61Q 17/005* (2013.01)
USPC ............ 510/441; 510/108; 510/238; 510/504

(58) Field of Classification Search
USPC .................... 510/108, 238, 504, 441
See application file for complete search history.

(56) References Cited

U.S. PATENT DOCUMENTS

| | | | |
|---|---|---|---|
| 3,283,357 | A | 11/1966 | Decker et al. |
| 3,547,828 | A | 12/1970 | Mansfield et al. |
| 3,692,618 | A | 9/1972 | Dorschner et al. |
| 3,726,395 | A | 4/1973 | Duhy |
| 3,849,241 | A | 11/1974 | Butin et al. |
| 4,041,203 | A | 8/1977 | Brock et al. |
| 4,096,311 | A | 6/1978 | Pietreniak |
| 4,273,661 | A * | 6/1981 | Grey ............... 510/518 |
| 4,340,563 | A | 7/1982 | Appel et al. |
| 4,448,704 | A * | 5/1984 | Barby et al. ......... 15/104.93 |
| 4,615,937 | A | 10/1986 | Bouchette |
| 4,692,374 | A | 9/1987 | Bouchette |
| 4,748,158 | A | 5/1988 | Biermann et al. |

(Continued)

FOREIGN PATENT DOCUMENTS

| | | |
|---|---|---|
| DE | 2513251 A1 | 9/1976 |
| GB | 1532072 | 11/1978 |

(Continued)

OTHER PUBLICATIONS

Lawrence, K.D. et al., "An Improved Device for the Formation of Superfine Thermoplastic Fibers," *NRL Report 5265*, Feb. 11, 1959.

(Continued)

*Primary Examiner* — Jane L Stanley
(74) *Attorney, Agent, or Firm* — Nancy M. Klembus; Ralph H. Dean, Jr.

(57) ABSTRACT

A dry wiper for use with disinfectant solutions having synthetic fibers and a disinfectant releasing treatment that makes the wiper active disinfectant stable is disclosed. Particularly, the wiper is stable for use in both quaternary ammonium disinfectant solutions and bleach disinfectant solutions. A method for producing such a wiper is also disclosed.

1 Claim, 11 Drawing Sheets

(56) References Cited

U.S. PATENT DOCUMENTS

| | | |
|---|---|---|
| 4,795,668 A | 1/1989 | Krueger et al. |
| 4,818,594 A | 4/1989 | Albien et al. |
| 4,820,577 A | 4/1989 | Morman et al. |
| 4,834,903 A | 5/1989 | Roth et al. |
| 4,929,498 A | 5/1990 | Suskind et al. |
| 4,941,989 A | 7/1990 | Kramer et al. |
| 4,946,617 A | 8/1990 | Sheridan et al. |
| 4,950,526 A | 8/1990 | Singleton |
| 5,004,760 A | 4/1991 | Patton et al. |
| 5,006,267 A | 4/1991 | Vaughn et al. |
| 5,057,368 A | 10/1991 | Largman et al. |
| 5,069,970 A | 12/1991 | Largman et al. |
| 5,091,102 A | 2/1992 | Sheridan |
| 5,094,770 A | 3/1992 | Sheridan et al. |
| 5,108,820 A | 4/1992 | Kaneko et al. |
| 5,108,827 A | 4/1992 | Gessner |
| 5,145,727 A | 9/1992 | Potts et al. |
| 5,151,321 A | 9/1992 | Reeves et al. |
| 5,169,706 A | 12/1992 | Collier, IV et al. |
| 5,178,931 A | 1/1993 | Perkins et al. |
| 5,188,885 A | 2/1993 | Timmons et al. |
| 5,196,139 A * | 3/1993 | Moschner ............... 252/186.25 |
| 5,277,976 A | 1/1994 | Hogle et al. |
| 5,284,703 A | 2/1994 | Everhart et al. |
| 5,294,482 A | 3/1994 | Gessner |
| 5,336,552 A | 8/1994 | Strack et al. |
| 5,350,624 A | 9/1994 | Georger et al. |
| 5,382,400 A | 1/1995 | Pike et al. |
| 5,389,202 A | 2/1995 | Everhart et al. |
| 5,466,410 A | 11/1995 | Hills |
| 5,540,992 A | 7/1996 | Marcher et al. |
| 5,576,284 A | 11/1996 | Van Buskirk et al. |
| 5,856,290 A | 1/1999 | Van Buskirk et al. |
| 6,103,061 A | 8/2000 | Anderson et al. |
| 6,107,268 A | 8/2000 | Yahiaoui et al. |
| 6,149,767 A | 11/2000 | Hermans et al. |
| 6,177,370 B1 | 1/2001 | Skoog et al. |
| 6,313,049 B1 | 11/2001 | Heady et al. |
| 6,331,230 B1 | 12/2001 | Hermans et al. |
| 6,340,663 B1 | 1/2002 | Deleo et al. |
| 6,346,125 B1 | 2/2002 | Mao |
| 6,417,154 B1 | 7/2002 | Yahiaoui et al. |
| 6,489,285 B2 | 12/2002 | Faber |
| 6,559,116 B1 | 5/2003 | Godfroid et al. |
| 6,599,521 B1 | 7/2003 | Resheski-Wedepohl |
| 6,627,612 B1 * | 9/2003 | O'Lenick et al. ............... 514/25 |
| 6,649,547 B1 | 11/2003 | Arnold et al. |
| 6,667,290 B2 | 12/2003 | Svendsen |
| 6,692,825 B2 | 2/2004 | Qin et al. |
| 6,712,121 B2 | 3/2004 | Clark et al. |
| 6,716,805 B1 | 4/2004 | Sherry et al. |
| 6,730,654 B2 | 5/2004 | Godfroid et al. |
| 6,734,157 B2 | 5/2004 | Radwanski et al. |
| 6,736,916 B2 | 5/2004 | Steinke et al. |
| 6,767,508 B1 * | 7/2004 | Yahiaoui et al. ............... 422/28 |
| 6,777,056 B1 | 8/2004 | Boggs et al. |
| 6,784,126 B2 | 8/2004 | Everhart et al. |
| 6,794,351 B2 | 9/2004 | Shick et al. |
| 6,794,352 B2 | 9/2004 | Svendsen |
| 6,797,360 B2 | 9/2004 | Varona |
| 6,797,377 B1 | 9/2004 | DeLucia et al. |
| 6,825,158 B2 | 11/2004 | Mitra et al. |
| 6,841,527 B2 | 1/2005 | Mitra et al. |
| 6,881,710 B1 * | 4/2005 | O'Lenick et al. ............. 510/123 |
| 2003/0194932 A1 | 10/2003 | Clark et al. |
| 2003/0216273 A1 * | 11/2003 | Mitra et al. ................... 510/295 |
| 2004/0048768 A1 | 3/2004 | Clark et al. |
| 2004/0209792 A1 | 10/2004 | Mitra et al. |
| 2004/0228904 A1 | 11/2004 | Ellis et al. |
| 2005/0025668 A1 * | 2/2005 | Katsigras et al. ............... 422/37 |
| 2005/0034255 A1 | 2/2005 | Svendsen |
| 2005/0047961 A1 * | 3/2005 | Bains et al. .................... 422/37 |
| 2005/0245151 A1 | 11/2005 | Annis et al. |
| 2006/0008538 A1 * | 1/2006 | Wu et al. ...................... 424/705 |
| 2006/0039956 A1 * | 2/2006 | Hensen et al. ................. 424/443 |

FOREIGN PATENT DOCUMENTS

| | | |
|---|---|---|
| WO | WO 86/05199 | 9/1986 |
| WO | WO 86/05509 | 9/1986 |
| WO | WO 95/09605 | 4/1995 |
| WO | WO 03/053144 | 7/2003 |
| WO | WO 2004/041312 | 5/2004 |
| WO | WO 2004/087226 | 10/2004 |

OTHER PUBLICATIONS

Manson, J.A. et al., *Polymer Blends and Composites*, Plenum Press, IBSN 0-306-30831-2, 1976, pp. 273-277.

Wente, B.A. et al., "Manufacture of Superfine Organic Fibers," *NRL Report 4364*, May 25, 1954.

* cited by examiner

WIPER FOR USE WITH DISINFECTANTS

BACKGROUND

Disinfectants are commonly used when cleaning surfaces to kill micro-organisms and reduce the possibility for infections. Quaternary ammonium chlorides (commonly referred to as "quats") are one of the most prevalent active pesticides used in disinfectants. The labels on disinfectants describe how to mix them for use and to apply them to surfaces by either saturating the surface or using a wiper, towel, sponge, or other substrate.

Quats are also commonly used as the active ingredient in sanitizers. By definition, "sanitizers" use a lower concentration of quat compounds than are used in "disinfectant" solutions. Typically, a sanitizer will only have 200-400 ppm of a quat in solution while a disinfectant will have about 600-3000 ppm of a quat in solution. As such, sanitizers are safe for cleaning surfaces used in food preparation (e.g., restaurants and kitchens), while disinfectants are used to clean surfaces in hospital environments.

The U.S. Environmental Protection Agency (EPA) requires that kill claims be substantiated by efficacy studies for the mixed liquid, but not for the liquid that is expressed from a dry wiper that is wetted by the user (rather than pre-saturated by the manufacturer). The problem is that a wiper may deplete 10-60% of the active quat from the disinfectant, depending on the materials making up the construction of the wiper. The active quats are adsorbed on to the surface of the wiper substrate. For example, cotton towels are prevalently used because of their absorbency. However, cotton towels deplete 60% from active quat from a quat-based disinfectant solution introduced to such a towel. Similarly, polyester wipers deplete around 10% of the quat from the disinfectant solution introduced into such a wiper. This reduction of active quats in a disinfectant solution decreased the effectiveness of the solution to kill harmful micro-organisms. The same type of problem is also encountered with sanitizer solutions.

For example, for a wiper or other substrate to be considered "disinfectant stable", the substrate must be capable of expressing 90 to 110 percent of the active disinfectant that has been introduced to the wiper from a disinfectant solution. Specifically, for a wiper to be considered "quat stable", that substrate must be capable of expressing 90-110% of the quats that are introduced to the substrate from the a quat-based disinfectant solution.

Pre-saturated wipers solve this problem by compensating the quat concentrations during the manufacturing process to be consistent with the label. As used herein, the term "pre-saturated" in reference to a wiper, refers to wipers that are saturated by the manufacturer with the desired liquid and delivered to the user in a wet format. However, for products that are delivered to the customer as a dry substrate to which the customer adds their own disinfectant solution, the level of quats in disinfectant solution cannot be increased. In such instances, the customer must rely on the substrate to release 100% of the quats from the substrate after the solution has been added to such a substrate.

Some have addressed this problem by taking advantage of the positive charge of the active quat ion in solution. For example, some have imparted a positive charge to the surface of substrates to repel the positive quat ions in solution. In the field of wipers for use with sanitizers, U.S. Pat. No. 6,667,290 to Svendsen uses an adhesive binder that is either positive or neutrally charged to give the article an overall positive charge to repel quat compounds in a sanitizer solution. It is also contemplated that a positively charged surfactant may also be used on such an article. However, such a solution looses its effectiveness with higher concentrations of quat ion as are present in disinfectant solutions.

Additionally, wipers currently available for use with disinfectants and/or sanitizers that address the problem of decreasing quat effectiveness are generally not stable in bleach solutions. In the same way as experienced with quat solutions, the active disinfectant of bleach solutions also adsorbs to untreated wiper substrates. This is problematic for most end users due to the frequent use of bleach solutions to disinfect or sanitize a surface. Even those who use quat solutions in some circumstances will often use bleach solutions in other circumstances and would like to use the same wiper product.

SUMMARY OF THE INVENTION

In view of the issues with wiper efficacy in disinfectant solutions, it is desired to have a wiper that is stable and compatible for use with disinfectant quat solutions and disinfectant bleach solutions.

The present invention is directed to a dry wiper for use with disinfectant solutions made of a dry substrate having synthetic fibers and a disinfectant release treatment present on the substrate and where the wiper is active disinfectant stable. In some embodiments the wiper is both quat stable and bleach stable.

In some embodiments the disinfectant release treatment is a quaternary ammonium compound, and more specifically may be a dialkyl dimethyl ammonium compound. More specifically, the disinfectant release treatment may be a N-,N-dialkyl-N,N-dimethylammonium X compound, where X is a chemical group such as a carbonate, bicarbonate, sulfate, methyl sulfate, or an ethyl sulfate. In one embodiment the disinfectant release treatment is didecyl dimethylammonium carbonate or didecyl dimethylammonium bicarbonate. In other embodiments the disinfectant release treatment may be a lauryldimethylammoniumhydroxypropyl alkyl polyglucoside.

In particular embodiments, the disinfectant release treatment may be present on the substrate at an add-on level of about 0.20 percent or less, based on the weight of the substrate. In another particular embodiment, the wiper also has a surfactant present on the wiper substrate.

In various embodiments, 100 percent of the fibers used in making the substrate may be synthetic fibers. In further embodiments, the substrate may be made from polypropylene fibers, polyethylene fibers, polyester fibers, or bicomponent fibers. In some embodiments the wiper substrate is melt-spun, drylaid, wetlaid, knitted, or woven. The wiper substrate may be pattern roll bonded, through-air bonded, or hydroentangled.

The invention is also directed to a wiper system for disinfecting surfaces having a wiper made of a dry substrate having synthetic fibers and a disinfectant release treatment present on the substrate such that the wiper is both quat stable and bleach stable. Additionally, the system has a disinfectant solution and a container that contains the wiper and into which the disinfectant solution may be introduced. In one embodiment the wiper of the system may be made from polypropylene fibers, polyethylene fibers, polyester fibers, or bicomponent combinations of such polymers. In another embodiment, the disinfectant solution is a quaternary ammonium disinfectant or a bleach solution disinfectant.

Finally, the invention is also directed to a method for producing a wiper for use with disinfectant solutions. The method consists of the steps of forming a dry substrate having synthetic fibers; and applying a disinfectant release treatment to the substrate which makes the wiper both quat stable and bleach stable. In some embodiments the disinfectant release treatment may be applied during the formation of the substrate. In other embodiments, the disinfectant release treatment may be applied to the synthetic fibers prior to formation of the substrate. In another embodiment, the disinfectant release treatment may be applied to the synthetic fibers after formation of the substrate.

In one embodiment, the method includes the step of heat treating the substrate after the substrate has been treated with the disinfectant release treatment.

In the interests of brevity and conciseness, any ranges of values set forth in this specification contemplate all values within the range and are to be construed as support for claims reciting any sub-ranges having endpoints which are whole number values within the specified range in question. By way of a hypothetical illustrative example, a disclosure in this specification of a range of from 1 to 5 shall be considered to support claims to any of the following ranges: 1-5; 1-4; 1-3; 1-2; 2-5; 2-4; 2-3; 3-5; 3-4; and 4-5.

Definitions

As used herein the term "nonwoven fabric or web" means a web having a structure of individual fibers or threads which are interlaid, but not in an identifiable manner as in a knitted fabric. Nonwoven fabrics or webs have been formed from many processes such as for example, meltblowing processes, spunbonding processes, and bonded carded web processes. The basis weight of nonwoven fabrics is usually expressed in ounces of material per square yard (osy) or grams per square meter (g/m$^2$ or gsm) and the fiber diameters useful are usually expressed in microns. (Note that to convert from osy to gsm, multiply osy by 33.91).

As used herein, the term "spunbond" and "spunbonded filaments" refers to small diameter continuous filaments which are formed by extruding a molten thermoplastic material as filaments from a plurality of fine, usually circular, capillaries of a spinnerette with the diameter of the extruded filaments then being rapidly reduced as by, for example, eductive drawing and/or other well-known spun-bonding mechanisms. The production of spunbonded nonwoven webs is illustrated in patents such as, for example, in U.S. Pat. No. 4,340,563 to Appel et al., and U.S. Pat. No. 3,692,618 to Dorschner et al. The disclosures of these patents are hereby incorporated by reference.

As used herein the term "meltblown" means fibers formed by extruding a molten thermoplastic material through a plurality of fine, usually circular die capillaries as molten threads or filaments into converging high velocity gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, in various patents and publications, including NRL Report 4364, "Manufacture of Super-Fine Organic Fibers" by B. A. Wendt, E. L. Boone and D. D. Fluharty; NRL Report 5265, "An Improved Device For The Formation of Super-Fine Thermoplastic Fibers" by K. D. Lawrence, R. T. Lukas, J. A. Young; and U.S. Pat. No. 3,849,241, issued Nov. 19, 1974, to Butin, et al As used herein, the term "bonded carded webs" refers to webs that are made from staple fibers which are usually purchased in bales. The bales are placed in a fiberizing unit/picker which separates the fibers. Next, the fibers are sent through a combining or carding unit which further breaks apart and aligns the staple fibers in the machine direction so as to form a machine direction-oriented fibrous non-woven web. Once the web has been formed, it is then bonded by one or more of several bonding methods. One bonding method is powder bonding wherein a powdered adhesive is distributed throughout the web and then activated, usually by heating the web and adhesive with hot air. Another bonding method is pattern bonding wherein heated calender rolls or ultrasonic bonding equipment is used to bond the fibers together, usually in a localized bond pattern through the web and or alternatively the web may be bonded across its entire surface if so desired. When using bi-component staple fibers, through-air bonding equipment is, for many applications, especially advantageous.

As used herein "multilayer laminate" means a laminate wherein one or more of the layers may be spunbond and/or meltblown such as a spunbond/meltblown/spunbond (SMS) laminate and others as disclosed in U.S. Pat. No. 4,041,203 to Brock et al., U.S. Pat. No. 5,169,706 to Collier, et al, U.S. Pat. No. 5,145,727 to Potts et al., U.S. Pat. No. 5,178,931 to Perkins et al. and U.S. Pat. No. 5,188,885 to Timmons et al. Such a laminate may be made by sequentially depositing onto a moving forming belt first a spunbond fabric layer, then a meltblown fabric layer and last another spunbond layer and then bonding the laminate in a manner described below. Alternatively, the fabric layers may be made individually, collected in rolls, and combined in a separate bonding step. Such fabrics usually have a basis weight of from about 0.1 to 12 osy (6 to 400 gsm), or more particularly from about 0.40 to about 3 osy. Multilayer laminates for many applications also have one or more film layers which may take many different configurations and may include other materials like foams, tissues, woven or knitted webs and the like.

As used herein, the term "polymer" generally includes but is not limited to, homopolymers, copolymers, such as for example, block, graft, random, and alternation copolymers, terpolymers, etc. and blends and modifications thereof. Furthermore, unless otherwise specifically limited, the term "polymer" includes all possible geometrical configurations of the molecule. These configurations include, but are not limited to isotactic syndiotactic, and random symmetries.

As used herein, the term "thermoplastic" refers to a polymer which is capable of being melt processed.

As used herein the term "monocomponent" fiber refers to a fiber formed from one or more extruders using only one polymer. This is not meant to exclude fibers formed from one polymer to which small amounts of additives have been added for color, antistatic properties, lubrication, hydrophilicity, etc. These additives, e.g. titanium dioxide for color, are generally present in an amount less than 5 weight percent and more typically about 2 weight percent.

As used herein the term "conjugate fibers" refers to fibers which have been formed from at least two polymers extruded from separate extruders but spun together to form one fiber. Conjugate fibers are also sometimes referred to as multicomponent or bicomponent fibers. The polymers are usually different from each other though conjugate fibers may be monocomponent fibers. The polymers are arranged in substantially constantly positioned distinct zones across the cross-section of the conjugate fibers and extend continuously along the length of the conjugate fibers. The configuration of such a conjugate fiber may be, for example, a sheath/core arrangement wherein one polymer is surrounded by another or may be a side by side arrangement, a pie arrangement or an "islands-in-the-sea" arrangement. Conjugate fibers are taught in U.S. Pat. No. 5,108,820 to Kaneko et al., U.S. Pat. No. 4,795,668 to Krueger et al., U.S. Pat. No. 5,540,992 to Marcher et al. and U.S. Pat. No. 5,336,552 to Strack et al.

Conjugate fibers are also taught in U.S. Pat. No. 5,382,400 to Pike et al. and may be used to produce crimp in the fibers by using the differential rates of expansion and contraction of the two (or more) polymers. Crimped fibers may also be produced by mechanical means and by the process of German Patent DT 25 13 251 A1. For two component fibers, the polymers may be present in ratios of 75/25, 50/50, 25/75 or any other desired ratios. The fibers may also have shapes such as those described in U.S. Pat. Nos. 5,277,976 to Hogle et al., U.S. Pat. No. 5,466,410 to Hills and 5,069,970 and 5,057,368 to Largman et al., which describe fibers with unconventional shapes.

As used herein the term "biconstituent fibers" refers to fibers which have been formed from at least two polymers extruded from the same extruder as a blend. The term "blend" is defined below. Biconstituent fibers do not have the various polymer components arranged in relatively constantly positioned distinct zones across the cross-sectional area of the fiber and the various polymers are usually not continuous along the entire length of the fiber, instead usually forming fibrils or protofibrils which start and end at random. Biconstituent fibers are sometimes also referred to as multiconstituent fibers. Fibers of this general type are discussed in, for example, U.S. Pat. Nos. 5,108,827 and 5,294,482 to Gessner. Bicomponent and biconstituent fibers are also discussed in the textbook *Polymer Blends and Composites* by John A. Manson and Leslie H. Sperling, copyright 1976 by Plenum Press, a division of Plenum Publishing Corporation of New York, IBSN 0-306-30831-2, at pages 273 through 277.

As used herein, the term "continuous filaments", refers to strands of continuously formed polymeric filaments having a length to diameter ratio of at least about a thousand and usually much higher. Such filaments will typically be formed by extruding molten material through a die head having a certain type and arrangement of capillary holes therein.

As used herein, the term "staple fiber", refers to a fiber that has been formed or cut to a staple lengths of generally 20 centimeters or less.

DETAILED DESCRIPTION

Figure 1:
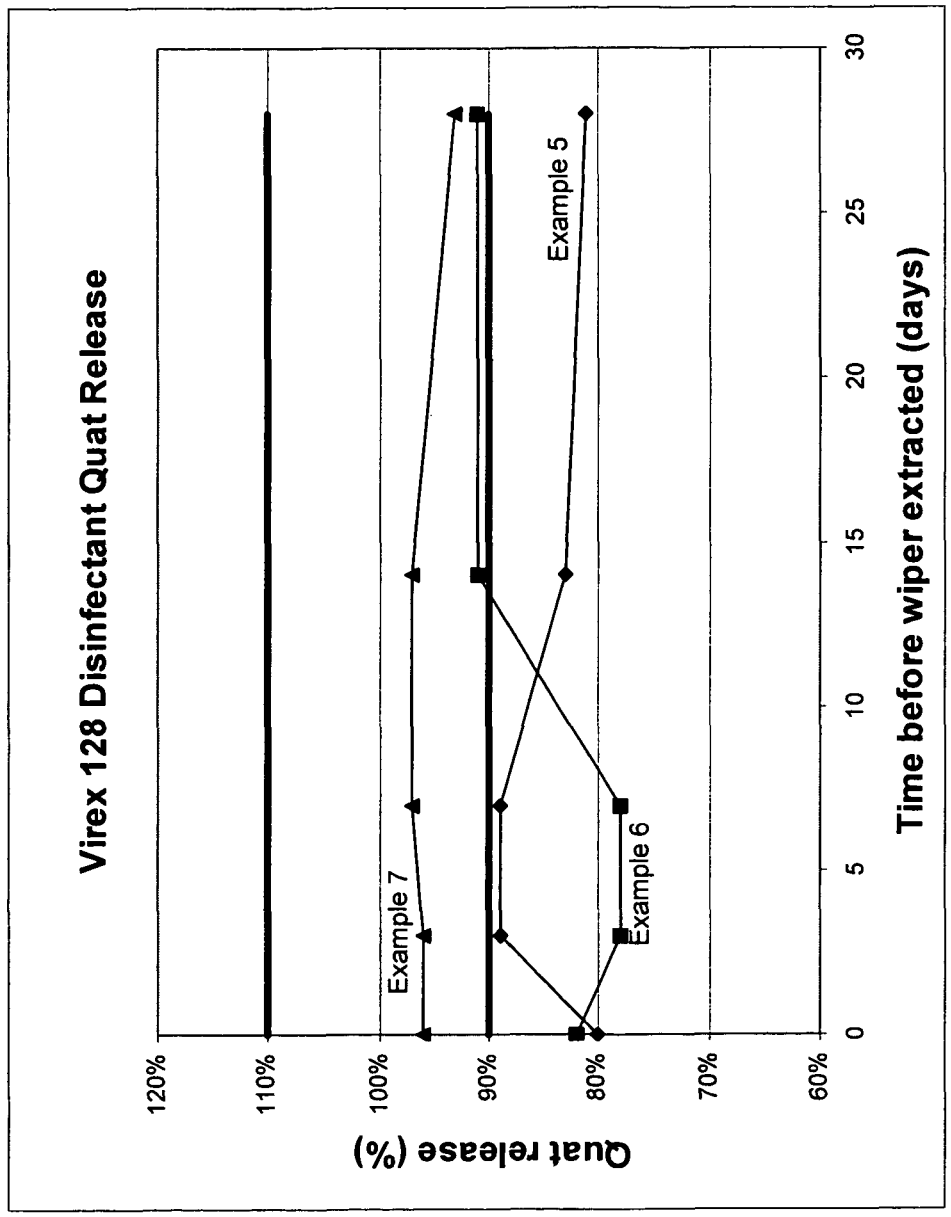
FIG. 1 is a plot of the percentage of active quat in the expressed solution from comparative example wipers at various testing time periods.
Figure 2:
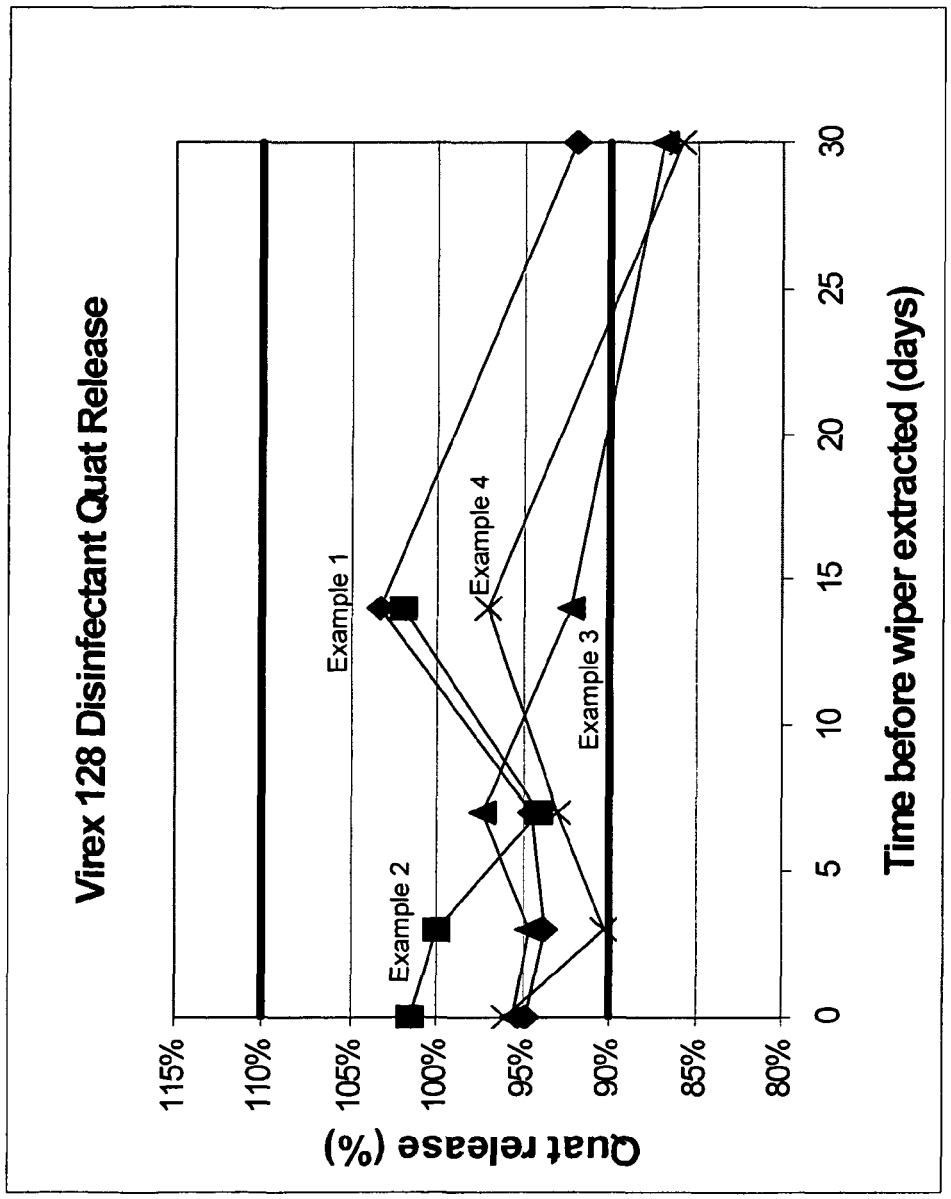
FIG. 2 is a plot of the percentage of active quat in the expressed solution from example wipers of the present invention at various testing time periods.
Figure 3:
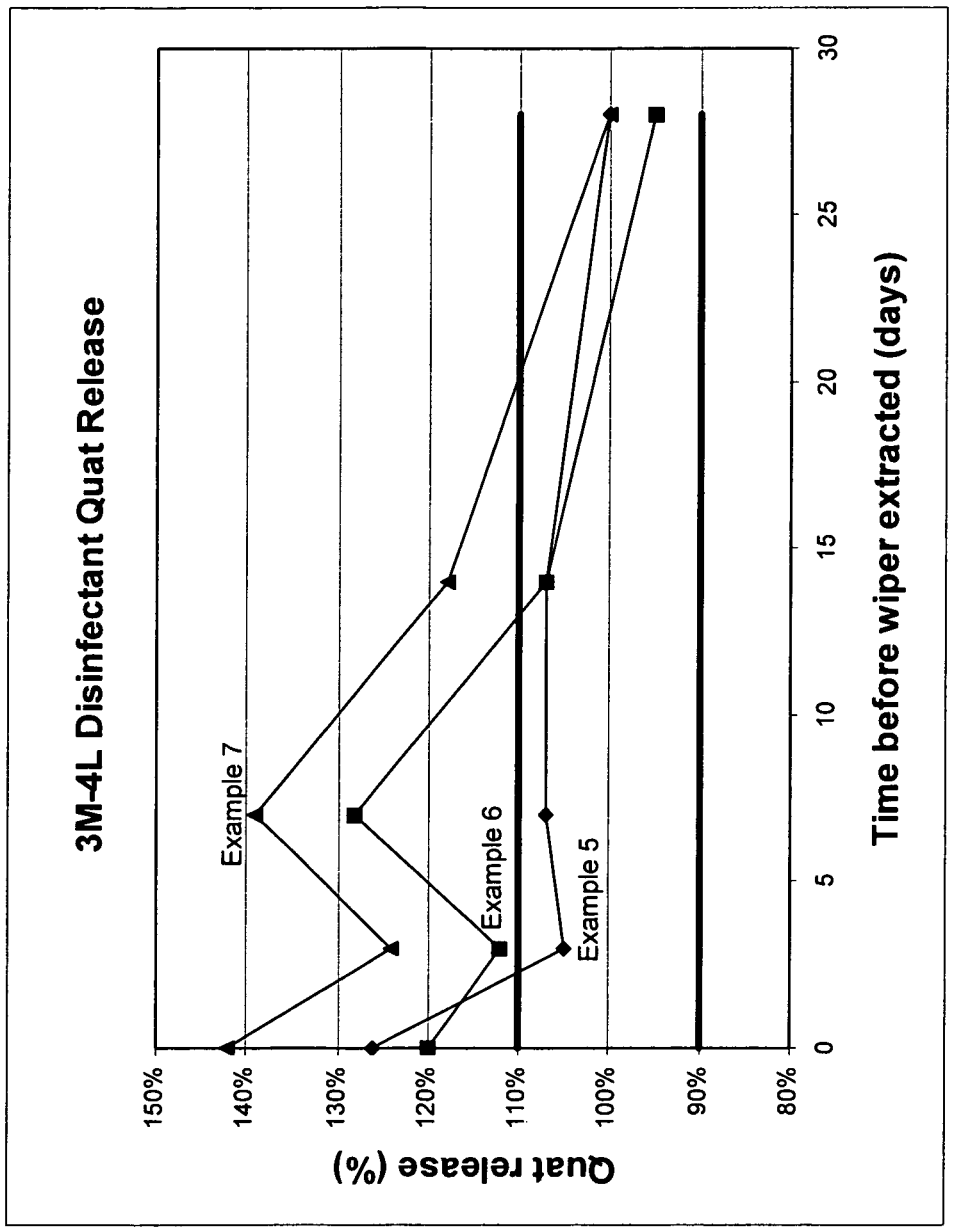
FIG. 3 is a plot of the percentage of active quat in the expressed solution from comparative example wipers at various testing time periods.
Figure 4:
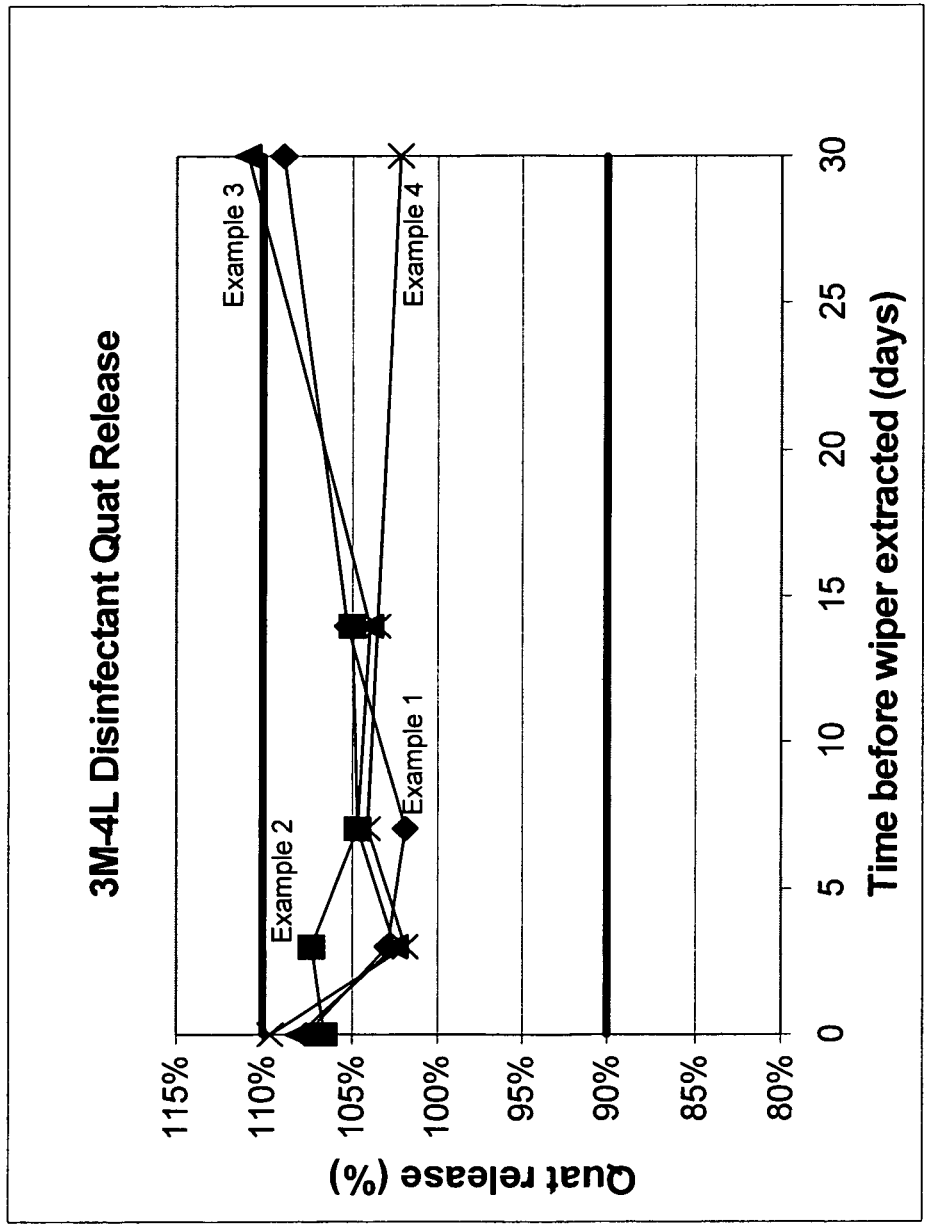
FIG. 4 is a plot of the percentage of active quat in the expressed solution from example wipers of the present invention at various testing time periods.
Figure 5:
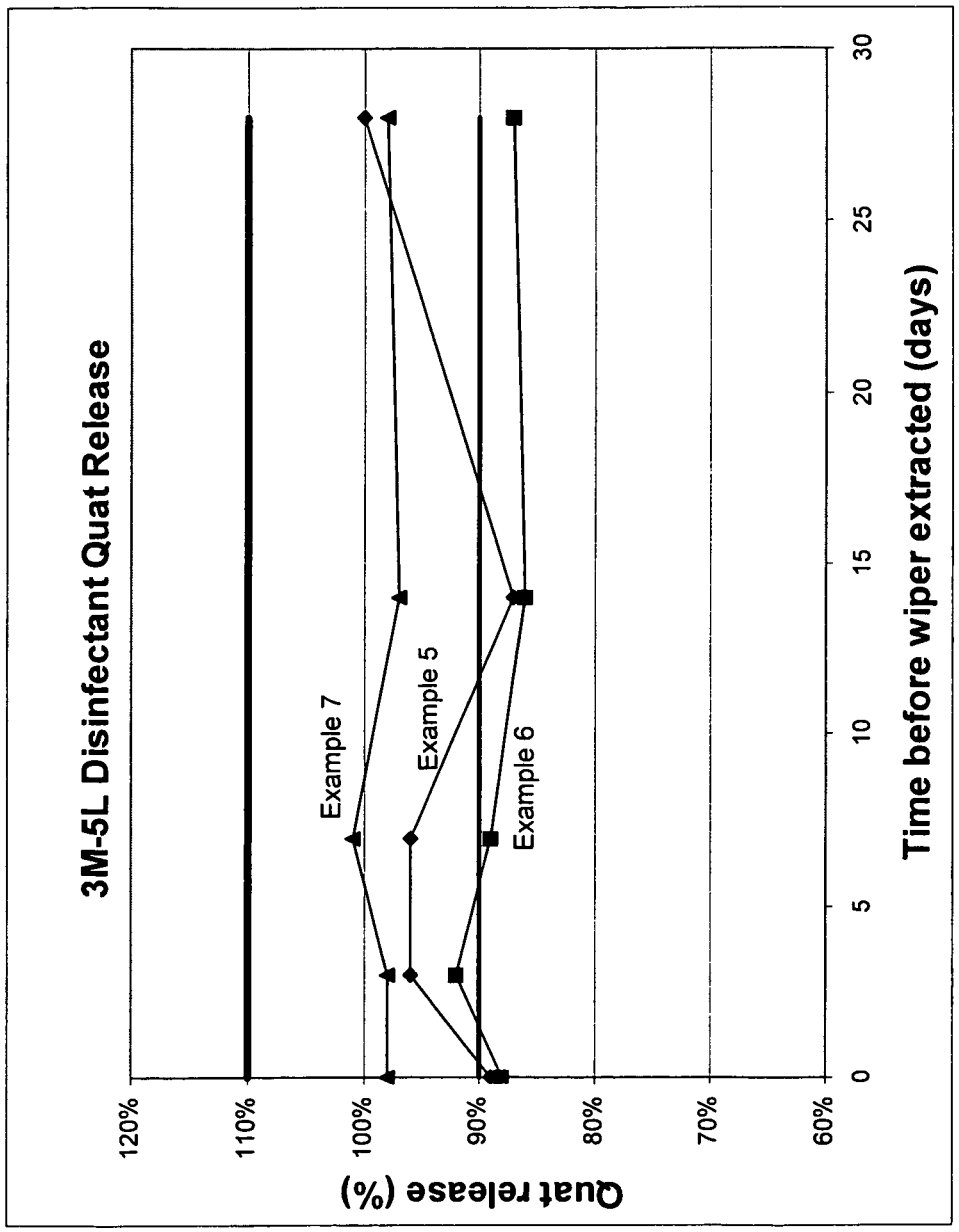
FIG. 5 is a plot of the percentage of active quat in the expressed solution from comparative example wipers at various testing time periods.
Figure 6:
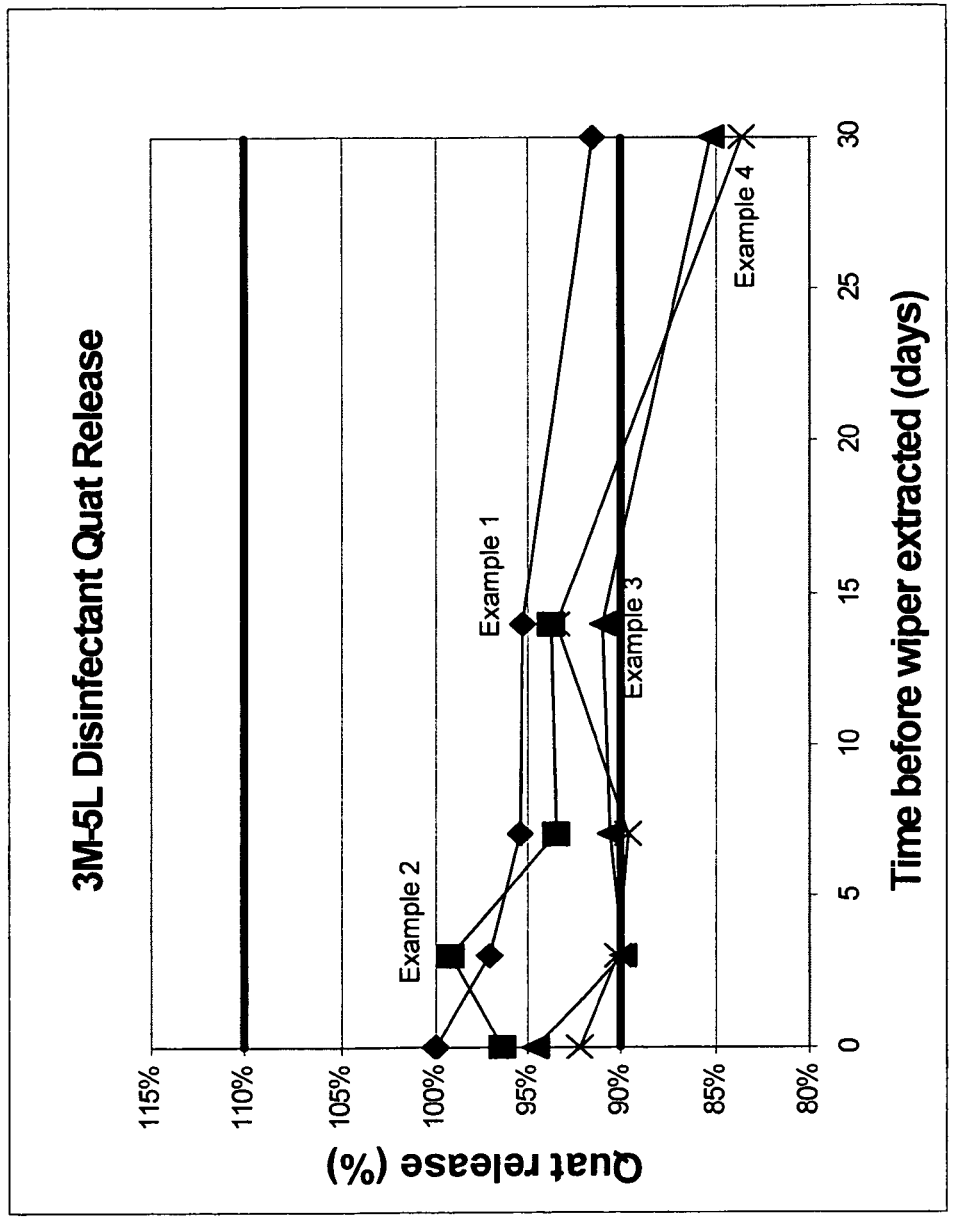
FIG. 6 is a plot of the percentage of active quat in the expressed solution from example wipers of the present invention at various testing time periods.
Figure 7:
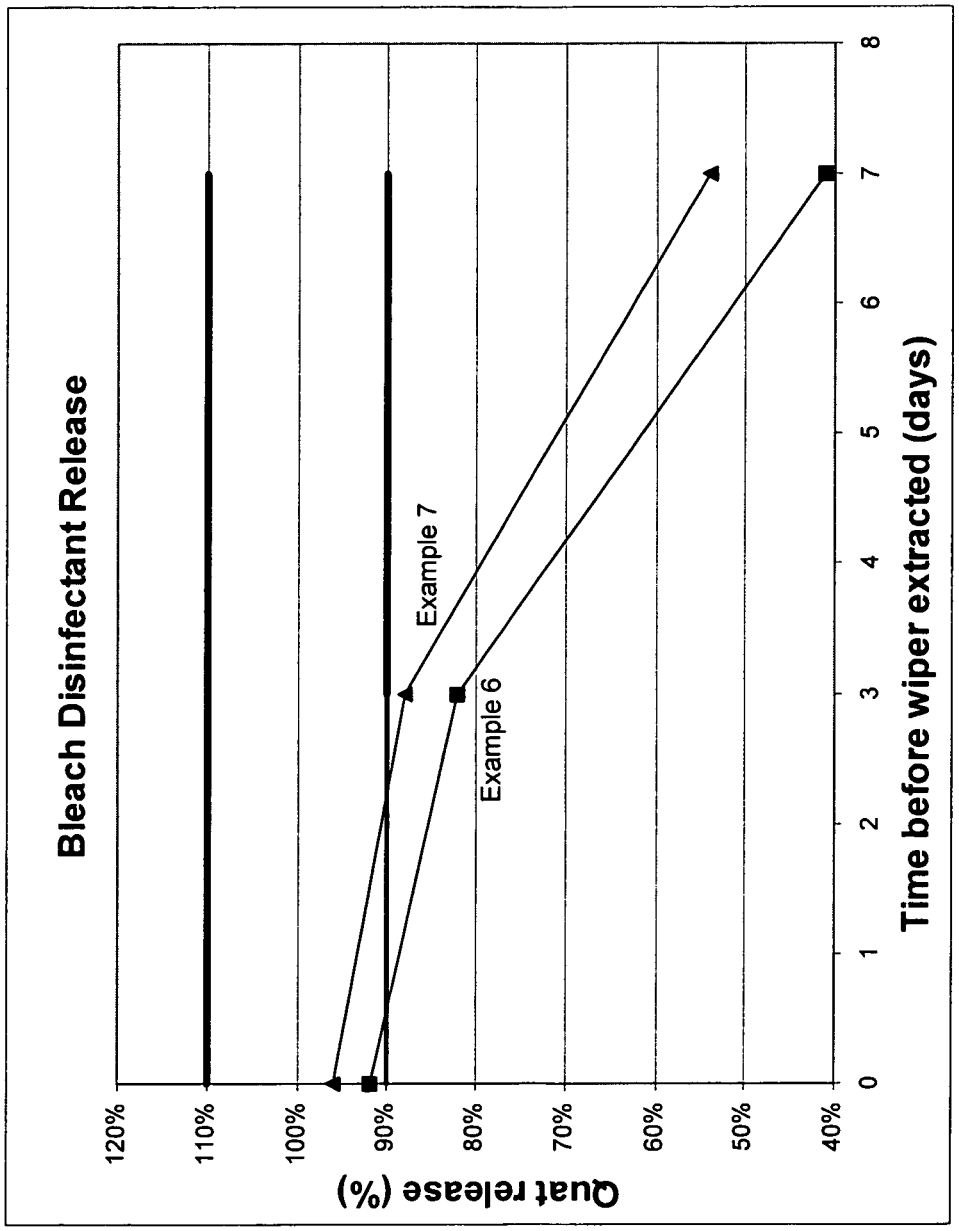
FIG. 7 is a plot of the percentage of active bleach disinfectant in the expressed solution from comparative example wipers at various testing time periods.
Figure 8:
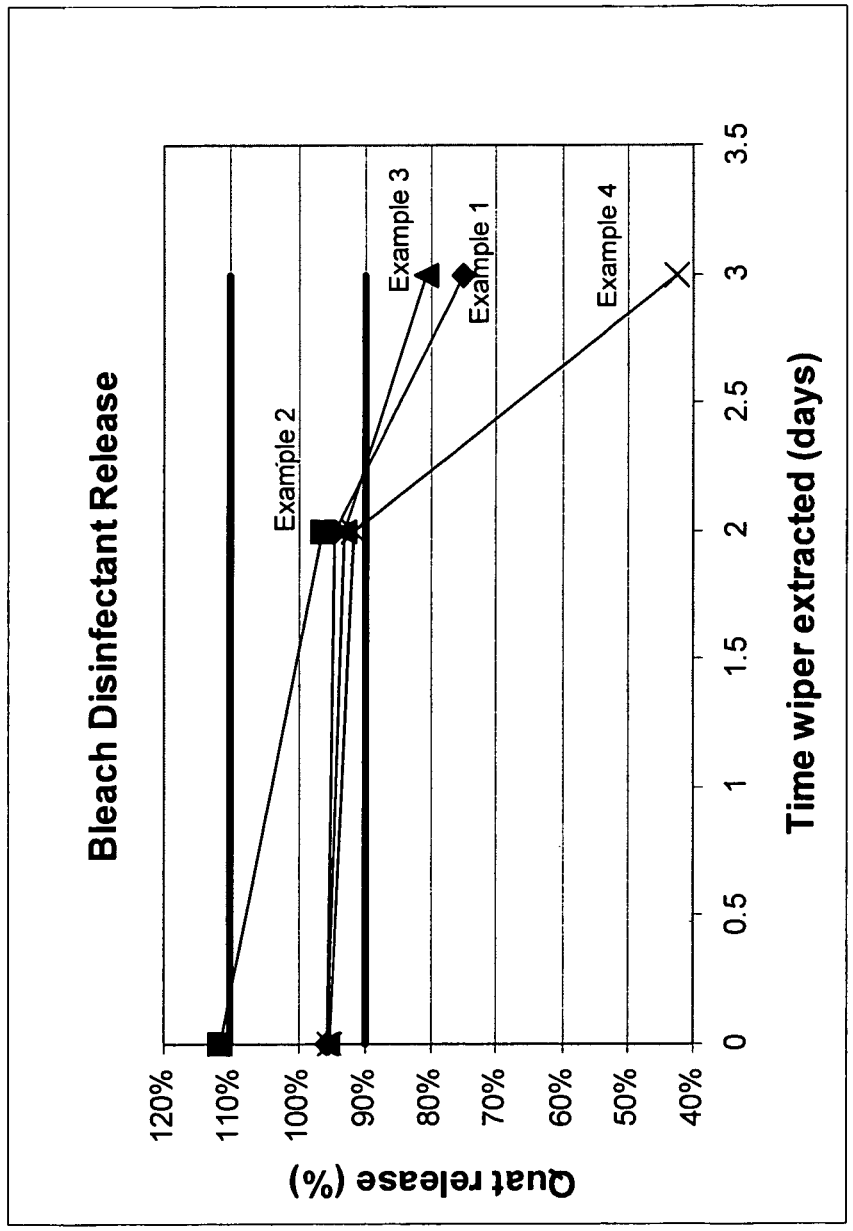
FIG. 8 is a plot of the percentage of active bleach disinfectant in the expressed solution from example wipers of the present invention at various testing time periods.

This invention is directed to wipers that are delivered to end users in a substantially dry format (i.e., not pre-saturated). The user may add or use their own disinfectant or sanitizing solution with the wipers to disinfect or sanitize surfaces. The end user may soak an individual wiper in their disinfectant solution or the disinfectant may instead by added to a collection of dry wipers such as to saturate the entire collection of wipers. An example of this type of execution is the WETTASK® system, available from Kimberly-Clark Corporation (Roswell, Ga.) where the user is provided with a roll of wipers and a bucket into which the user may pour their disinfectant, sanitizing or other cleanser to saturate the wiper. The saturated wipers may then be used to disinfect, sanitize or otherwise clean surfaces.

The dry wipers may be provided to the end user in any format that is useful to the user. The wipers may be delivered to the end user as an individual wiper, as a stack of individual wipers, as a stack of folded wipers, as a roll of wipers, or any other format that meets the specific needs of the user. Additionally, the wiper may be provided to the user with specialized packaging to facilitate the use of the wiper with the user's disinfectant, sanitizing and/or cleansing solutions. For example, the WETTASK® system is delivered to the user with a bucket into which the solutions and a roll of wipers may be placed.

The wipers of the present invention are made from fibers that are appropriate for the end use of the wiper. The fibers may be relatively short, staple length fibers, typically less than 3 inches, or longer and substantially more continuous fibers such as are produced by meltspinning process (i.e., spunbonding and meltblowing processes). It is preferable that the wipers be made from synthetic fibers such as polyesters, nylons, polypropylenes, polyethylenes, acrylics, polyvinyls, polyurethanes, and other such synthetic fibers as are well known. Suitable polyolefins include, but are not limited to, polyethylene, polypropylene, polybutylene, and the like; suitable polyamides include, but are not limited to, nylon 6, nylon 6/6, nylon 10, nylon 12 and the like; and suitable polyesters include, but are not limited to, polyethylene terephthalate, polybutylene terephthalate and the like.

The wipers may additionally have more than one type of fiber, may have biconstituent fibers, or may have conjugate fibers. Additionally, while it is preferred that synthetic fibers are used in the wipers of the present invention, natural fibers such as cellulosic materials may also be present. Similarly, regenerated cellulosic fibers such as rayon may be present in the wipers of the present invention as an addition to the synthetic fibers.

The process used to make the wipers of the present invention are generally well known in the industry. Such wipers are generally produced in a myriad of well known ways. Wipers can be made by woven, knitted, wet-formed, dry-formed, and nonwoven manufacturing processes. These processes may include, but is not limited to, spunbonding, meltblowing, staple fiber bonded carded web, air laying processes, wet laying processes, solution spinning, pattern-roll bonding, through-air bonding, and hydroentangling.

Wipers can be made of substrate webs that are a single layer web or may be made of substrate webs made of multiple layers. A substrate web made of multiple layers may have similar materials in each layer or may be made of differing layers. The wiper may be a mulilayer laminate.

It is intended that the substrate webs of the present invention be substantially dry and the resulting wiper be substantially dry when delivered to the user. As used herein, the term "substantially dry" refers to the web being free of liquid and all but ambient moisture.

Examples of materials that can be used for the wipers of the present invention are disclosed in U.S. Pat. No. 4,820,577 to Morman et al., U.S. Pat. No. 4,950,526 to Singleton, U.S. Pat. No. 5,350,624 to Georger et al., U.S. Pat. No. 6,331,230 to Hermans et al., U.S. Pat. No. 6,149,767 to Hermans et al., U.S. Pat. No. 6,177,370 to Skoog et al., U.S. Pat. No. 6,649,547 to Arnold et al., U.S. Pat. No. 6,692,825 to Qin et al., U.S. Pat. No. 6,736,916 to Steinke et al., U.S. Pat. No. 6,777,056 to Boggs et al., U.S. Pat. No., U.S. Pat. No. 6,797,360 to Varona, and U.S. Pat. No. 6,797,377 to DeLucia et al.

One example of a material that may used for the wiper of the invention are the hydroentangled materials commonly used in such wipers and sold by the Kimberly-Clark Corporation, Roswell, Ga., as HYDROKNIT®. Examples of such hydroentangled materials are discussed in U.S. Pat. No. 5,284,703 to Everhart et al., U.S. Pat. No. 5,389,202 to Everhart et al., U.S. Pat. No. 6,103,061 to Anderson et al., and U.S. Pat. No. 6,784,126 to Everhart et al.

It is intended that the wipers of the present invention be suitable for use with disinfectants, sanitizers, and cleansers that are commonly used for the disinfecting, sanitizing, and cleansing of surfaces. As discussed above, most commonly available disinfectants and sanitizers use a quaternary ammonium chloride ("quat") compound as an active disinfectant in the disinfectant solution. Examples of such disinfectant solutions include "Virex 11128 One-Step Disinfectant Cleaner and Deodorant" available from JohnsonDiversey, Inc. (Sturtevant, Wis.). Other solutions with quat disinfectants are available from 3M (St. Paul, Minn.) and sold under the trade designation of "5L 3M™ Quat Disinfectant Cleaner 5L (Product No. 5)" and "4L 3M™ Bathroom Disinfectant Cleaner 4L (Product No. 4)".

Sodium hypochlorite bleach solutions are another common disinfectant. Such solutions are well known and are commonly available from many suppliers.

The present invention provides a wiper that can be used with such common disinfectants without appreciably decreasing the efficacy of the active disinfectant of the solution. The wiper is considered to be stable with such common disinfectant solutions. Specifically, the addition of a disinfectant release treatment to the wiper of the present invention prevents the active disinfectant of a disinfectant solution from being adsorbed on the wiper. As used herein, the term "stable" in reference to the use of the wiper with disinfectant solutions, refers wiper being capable of expressing between about 90 and 110 percent of the active disinfectant that is introduced in solution to the wiper. It is also desired that the wiper remain stable over a period of time that such wipers would be expected to be exposed to such disinfectant solutions (e.g., the time a roll of such wipers would be sitting in a bucket with the disinfectant solution).

It should be noted that although the discussion of "stability" here has been in reference to disinfectant solutions, the characteristic would also extend to sanitizing solutions. It is reasonable to conclude that a wiper that is stable for the higher concentrations of active component present in disinfectant solutions (i.e., more active component available to adsorb to the wiper) will also be stable for the lower concentrations of that same active ingredient present in a sanitizing solution (i.e., less active component available to adsorb to the wiper).

One of the disinfectant release treatments that has been found to be stable in both quat and bleach disinfectants are dialkyl dimethylammonium compounds. One specific type of dialkyl dimethylammonium compound that has been found to be useful for the present invention are dialkyl dimethylammonium carbonate and bicarbonate compounds. These dialkyl dimethylammonium compounds have either a carbonate or bicarbonate subgroup and are often both found in solution. One specific compound is the didecyl dimethylammonium carbonate/bicarbonate solution available from Lonza Inc. (Fair Lawn, N.J.) and sold under the trade designation of Carboquat® 22C50. (Previously, the primary use of Carboquat® compounds has been as a fungicide/insecticide lumber treatment.) Similarly, the dialkyl dimethlyammonium compound may have sulfate groups, such as sulfate, methylsulfate, or ethylsulfate groups, rather than carbonate or bicarbonate groups.

Another class of disinfectant release treatments that has been found to be stable in both quat and bleach disinfectants are alkyl polyglucoside ammonium compounds. Such compounds are derived from short to long alkyl chain sugars where the sugar or alkyl polyglucoside backbone is quaternized. An example of such a compound would be lauryldimethylammoniumhydroxypropyl alkyl polyglucosides such as sold by Colonial Chemical, Inc. (South Pittsburg, Tenn.) under the trade designation of Suga®Quat L-1010, L-1210, and L-8610. (Previously, the primary use of the SugaQuat® compounds has been as a skin and hair conditioner for use in personal care formulations.)

While the inventors do not intend to be limited to any one theory of operation, it is believed that disinfectant release treatments of the present invention prevent the adsorbsion of the active disinfectants by two mechanisms. These mechanisms are based on the disinfectant release treatment having a cation group and a large anion group. In the first mechanism, the cationic nature of disinfectant release treatment of the present invention electrochemically repels the active disinfectants. In the second mechanism, the unique physical geometry of the disinfectant release treatments of the present invention hinders the active disinfectant of the disinfectant solution from adsorbing on the wiper. As such, the disinfectant release treatments of the present invention are capable of providing the wiper with the ability to remain stable in either a quat-based disinfectant solution or a bleach-based disinfectant solution.

It is believed that other similar disinfectant release treatments may also be possible based on these mechanisms and may provide similar quat and bleach stability to a wiper. Other similar treatments having both the ability to electrochemically repel active disinfectants and geometrically hinder them from adsorbing to the wiper substrate may be similarly developed. For example, imidazolinium compounds, such as imidazolinium methyl sulfate, should also provide similar quat and bleach disinfectant stability, particularly when the anion component of the compounds are the chemical groups discussed above (i.e., carbonate, bicarbonate, sulfate, methyl sulfate, ethyl sufate, etc.).

The disinfectant release treatment may be added to the wipers of the invention by any method suitable for adding such treatments to substrates are well known. The treatment may be added to staple fibers prior to conversion into substrates or it may be incorporated into the fiber during melt-extrusion of the fibers. Similarly, the treatment may be added to the wiper substrate webs at any point during the production of the substrate webs. The treatment may be applied by any of the many well-known processes which include, but are not intended to be limited to spray application, gravure printing, brush, foam, slot dye, dip-and-squeeze, saturation, or other similar processes.

Typically, the disinfectant release treatment will be applied to the wiper substrate at an add-on level of less than 0.20 percent per weight of the wiper. More preferably, the disinfectant release treatment will be present in amount between about 0.05 percent and about 0.20 percent. More preferable, the disinfectant release treatment will be present in an amount between about 0.08 percent and 0.15 percent.

Optionally, the wipers of the present invention may also incorporate other compounds in addition to the disinfectant release treatment. Such additional compounds may be any such compounds that enhance the functionality or aesthetics of the wiper. For example, such optional compounds may include, but are not limited to, surfactants, pH buffers, chelating agents, anti-microbial agents, and the like.

Additionally, it has been surprisingly found that wipers having the disinfectant release treatment of the present invention are improved with some degree of heat annealing. It has been found that subjecting finished wipers of the present invention to a slightly elevated temperature decreases the variability in the efficiency of the wiper's ability to release active disinfectants. It is preferable that this heat annealing be conducted at a temperature greater than about 25 degrees C. and less than about 100 degrees C. More preferably the heat annealing be conducted at a temperature between about 38 degrees C. and 65 degrees C. It is also preferable that the wipers of the present invention be exposed to these elevated temperatures for less than about 45 days. More preferably the wipers of the present invention will be exposed to the elevated temperatures for about 14 days or less.

EXAMPLES

Examples 1-7

Polypropylene (PP) meltblown material (100 percent PP) was made on a pilot line and was treated with various disinfectant release treatments of the present invention. The PP meltblown material was made to a target basis weight of 1 oz/yd$^2$ (33.91 grams/m$^2$). The disinfectant release treatment was sprayed directly into the fiber bundle of the meltblown process between the exit slot of the dye tip and the traveling forming wire on which the meltblown fibers were collected to form the meltblown web. The meltblown web was then bonded with a 350 degree F. (177 degree C.) thermal bond dot patterned calender. A vacuum (18-21 inches H$_2$O) below the forming wire further consolidated the fibers and pulled any excess treatment solution through the fibrous web.

The PP meltblown material was perforated for 12-inch (308 mm) wide by 12.5-inch (318 mm) long wipers, v-folded and rolled-up without a core in a center flow dispensing configuration. The finished rolls were approximately 6 inches (154 mm) in height and approximately 6 inches (154 mm) in diameter.

Three different disinfectant release treatments of the present invention were used to produce the wipers of Examples 1-4, as described in Table 1. Examples 1 and 2, were two different add-on levels of Carboquat® 22C50. Example 3 was produced in the same way with SugaQuat® L1010. Example 4 was produced in the same way with SugaQuat® L8610.

Additionally, three comparison codes were also produced (Example 5-7). Example 5 was the PP meltblown web without any treatment added. Example 6 was made with a Glucopon 220UP surfactant, available from Cognis Corp. (Cincinnati, Ohio). Example 7 was made with quaternary ammonium chloride compound, Bardac® 2280, available from Lonza Inc.

TABLE 1

| Example | Treatment | Add-on level (%) |
| --- | --- | --- |
| 1 | Carboquat 22C50 | 0.08 |
| 2 | Carboquat 22C50 | 0.10 |
| 3 | SugaQuat L1010 | 0.12 |
| 4 | SugaQuat L8610 | 0.08 |
| 5 | None | N/A |
| 6 | Glucopon 220UP | 0.70 |
| 7 | Bardac 2280 | 0.10 |

Testing

To evaluate the efficiency of the wipers of the present invention to release active disinfectant, rolls were first saturated with disinfectant solution having a known active disinfectant concentration. Sample wipers were then removed from the rolls and the disinfectant solution expressed from the wiper. The expressed disinfectant solution was then analyzed and the concentration of expressed active disinfectant was compared with the active disinfectant concentration initially supplied to the wiper roll.

Four different disinfectant solutions were used in the testing of the wipers of the present invention: 1) Virex 128 from JohsonDiversey, Inc. (Sturtevant, Wis.), 2) 3M-4L from 3M (St. Paul, Minn.); 3) 3M-5L from 3M (St. Paul, Minn.); and 4) chlorine bleach from Clorox (Oakland, Calif.). Each of the disinfectants were made to specific concentrations by dilution with deionized water. The dilution ratios of disinfectant to water were: 1) Virex 128, 1 to 128; 2) 3M-4L, 1 to 59; 3) 3M-5L, 1 to 256; and 4) bleach, 1 to 24.

The sample wiper roll was placed in 1.2-gallon (4.54 L) bucket having a screw top lid and lid dispensing port, the roll placed in the bucket such that the non-folded edge of the roll faced upwards. An amount of 0.5 gallons (1.89 L) of the test disinfectant solution was then poured on to the roll being careful to avoid pouring the solution down the open roll core (center) or the perimeter space between the roll and the bucket. The lid was then placed on the bucket. Additionally, 0.5 gallons of the same test disinfectant solution was retained as a control.

Samples were taken from such test buckets at time periods of 1 hour, 3 days, 7 days, 14 days and 28 days. For each sampling period, ten wipers were removed through the dispensing port of the bucket and placed a large resealable plastic bag. The bag was then squeezed to obtain about 120 mL of the disinfectant solution contained within the saturated sample wipers. The expressed disinfectant solution was then analyzed for active disinfectants. The plastic bag and sample wipers were then discarded. As a control, a similar amount of disinfectant solution was also removed from the control sample at the same testing intervals.

The quaternary amine present in both the solution expressed from the wipers and in the control sample was determined by a back-titration utilizing a surfactant electrode and an auto-titrator. In the back-titration, excess (10 mL) sodium lauryl sulfate solution (0.005M) was added to a 25 mL aliquot of the solution sample, along with 70 mL of distilled water, and then titrated with benzethonium chloride (0.005M). Three titrations were performed for each 120 mL sample of expressed solution.

The back-titration was completed using an auto-titrator, Model 736CP Titrino and auto-sampler, Model 730 Sample Changer, and utilizing Brinkmann Titrino Workcell version 4.0 software, all available from Metrohm Ltd. (Herisau, Switzerland). An Orion Model 93-42 Surfactant Electrode and an Orion Model 90-02 Double Junction Reference Electrode, both available from Thermo Electron Corporation (Waltham, Mass.) were also used.

The percentage of disinfectant expressed was then calculated by dividing the quaternary amine concentration present in the expressed from the wiper divided by the quaternary amine concentration present in the control sample.

Similarly, the sodium hypochlorite present in both the solution expressed from the wiper saturated in the bleach solution and in the control sample was determined by a redox titration. In the redox titration, 60 mL of 3.33 percent acetic acid and 10 mL of 1.0N potassium iodide were added to a 25 mL aliquot of the solution sample. A deep rust color developed and with stirring, the mixture was titrated with 0.1N sodium thiosulfate standard until a light yellow color appeared. Approximately 3 to 4 ml of 0.3% starch indicator was added and a deep purple color developed. Dropwise, the mixture was titrated to a colorless endpoint.

As with the quaternary amine testing, the percentage of disinfectant expressed was then calculated by dividing the sodium hypochlorite concentration present in the expressed from the wiper divided by the sodium hypochlorite concentration present in the control sample.

Rolls of each of the Examples were tested with each the four disinfectant solutions. Tables 2, 3, 4 and 5 give the results for the percentage of disinfectant expressed testing for the Virex 128, 3M-4L, 3M-5l and bleach disinfectant solutions, respectively. Additionally, the results are plotted in FIGS. 1 to 8 for each of the disinfectant solutions. The Examples using the disinfectant release treatment of the present invention (Examples 1 to 4) are plotted in FIGS. 2, 4, 6, and 8. The comparative Examples (Examples 5 to 7) are plotted in FIGS. 1, 3, 5, and 7. It should be noted that no results are given for Comparative Example 1 for the bleach solution because the PP meltblown material would not absorb any of the solution and thus there was no expressed solution to test.

TABLE 2

Quat Release for Virex 128 Disinfectant

| Example | Time of Extraction | | | | |
|---|---|---|---|---|---|
| | 0 days | 3 days | 7 days | 14 days | 28 days |
| 1 | 95% | 94% | 94% | 103% | 92% |
| 2 | 102% | 100% | 94% | 102% | |
| 3 | 96% | 95% | 97% | 92% | 87% |
| 4 | 96% | 90% | 93% | 97% | 86% |
| 5 | 80% | 89% | 89% | 83% | 81% |
| 6 | 82% | 78% | 78% | 91% | 91% |
| 7 | 96% | 96% | 97% | 97% | 93% |

TABLE 3

Quat Release for 3M-4L Disinfectant

| Example | Time of Extraction | | | | |
|---|---|---|---|---|---|
| | 0 days | 3 days | 7 days | 14 days | 28 days |
| 1 | 108% | 103% | 102% | 105% | 109% |
| 2 | 107% | 107% | 105% | 105% | |
| 3 | 108% | 102% | 105% | 104% | 111% |
| 4 | 110% | 102% | 104% | 103% | 102% |
| 5 | 126% | 105% | 107% | 107% | 100% |
| 6 | 120% | 112% | 128% | 107% | 95% |
| 7 | 142% | 124% | 139% | 118% | 100% |

TABLE 4

Quat Release for 3M-5L Disinfectant

| Example | Time of Extraction | | | | |
|---|---|---|---|---|---|
| | 0 days | 3 days | 7 days | 14 days | 28 days |
| 1 | 100% | 97% | 95% | 95% | 92% |
| 2 | 96% | 99% | 93% | 94% | |
| 3 | 95% | 90% | 91% | 91% | 85% |
| 4 | 92% | 90% | 90% | 94% | 84% |
| 5 | 89% | 96% | 96% | 87% | 100% |
| 6 | 88% | 92% | 89% | 86% | 87% |
| 7 | 98% | 98% | 101% | 97% | 98% |

TABLE 5

Bleach Disinfectant Release

| Example | Time of Extraction | | |
|---|---|---|---|
| | 0 days | 3 days | 7 days |
| 1 | 96% | 94% | 75% |
| 2 | 112% | 96% | |
| 3 | 96% | 93% | 81% |
| 4 | 95% | 92% | 43% |
| 5 | * | * | * |
| 6 | 92% | 82% | 41% |
| 7 | 96% | 88% | 54% |

As can be seen from the results in Tables 2 to 5 and in FIGS. 1 to 8, the Examples of the present invention were the only codes that were capable of expressing between about 90 percent and 110 percent of the active disinfectant introduced to the wiper. The Examples produced with the Carboquat® treatment (Examples 1 and 2) performed slightly better than the Examples produced with the SugQuat® treatment (Examples 3 and 4).

While the comparative Examples (Examples 5-8) had acceptable results for some of the disinfectant solutions, none were able to produce acceptable results in both the quat-based disinfectant solutions (Virex 128, 3M-4L, 3M-5L) and the bleach disinfectant solution.

Additionally, rolls of the wipers of Example 2 were further aged in a 130 degree F. (55 degrees C.) room for a total of 45 days. Sample rolls were removed from the heated room after 7 days, 14 days and after 45 days. Each heat-aged roll removed at these sample periods were then tested over a 28-day period for percentage quat release by the method discussed above. The results are plotted in FIGS. 9, 10 and 11.

Figure 9:
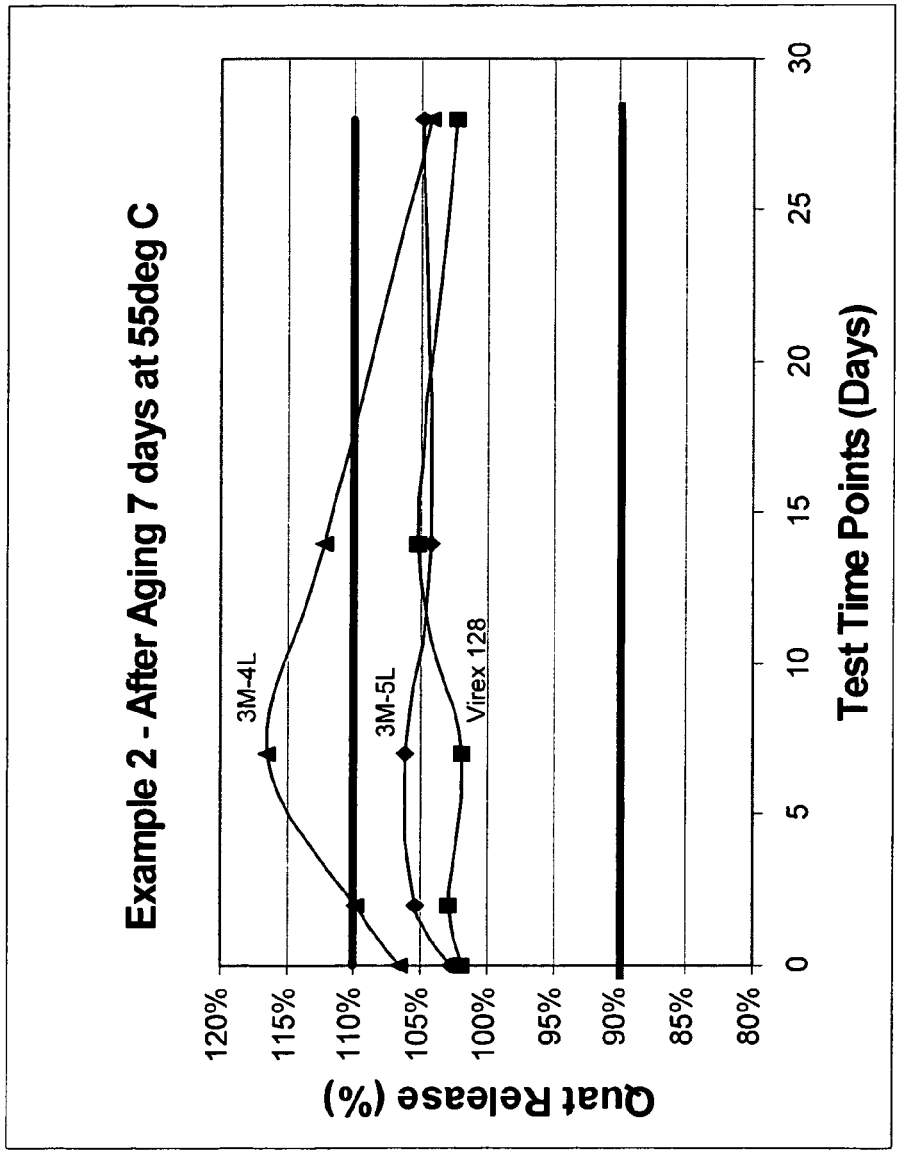
FIG. 9 is a plot of the percentage active disinfectant in the expressed solution, at various testing time periods, from a wiper of the present invention aged for 7 days at 55 degrees C. for different disinfectant solutions.
Figure 10:
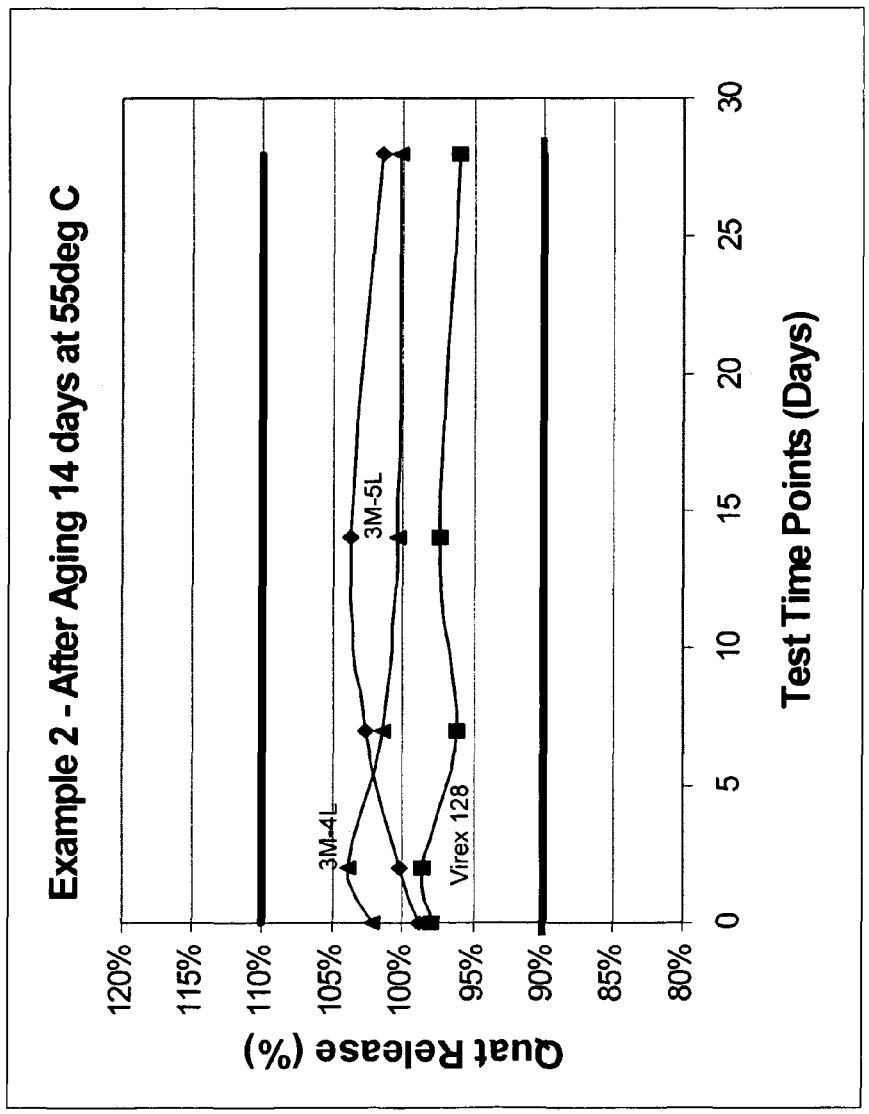
FIG. 10 is a plot of the percentage active disinfectant in the expressed solution, at various testing time periods, from a wiper of the present invention aged for 14 days at 55 degrees C. for different disinfectant solutions.
Figure 11:
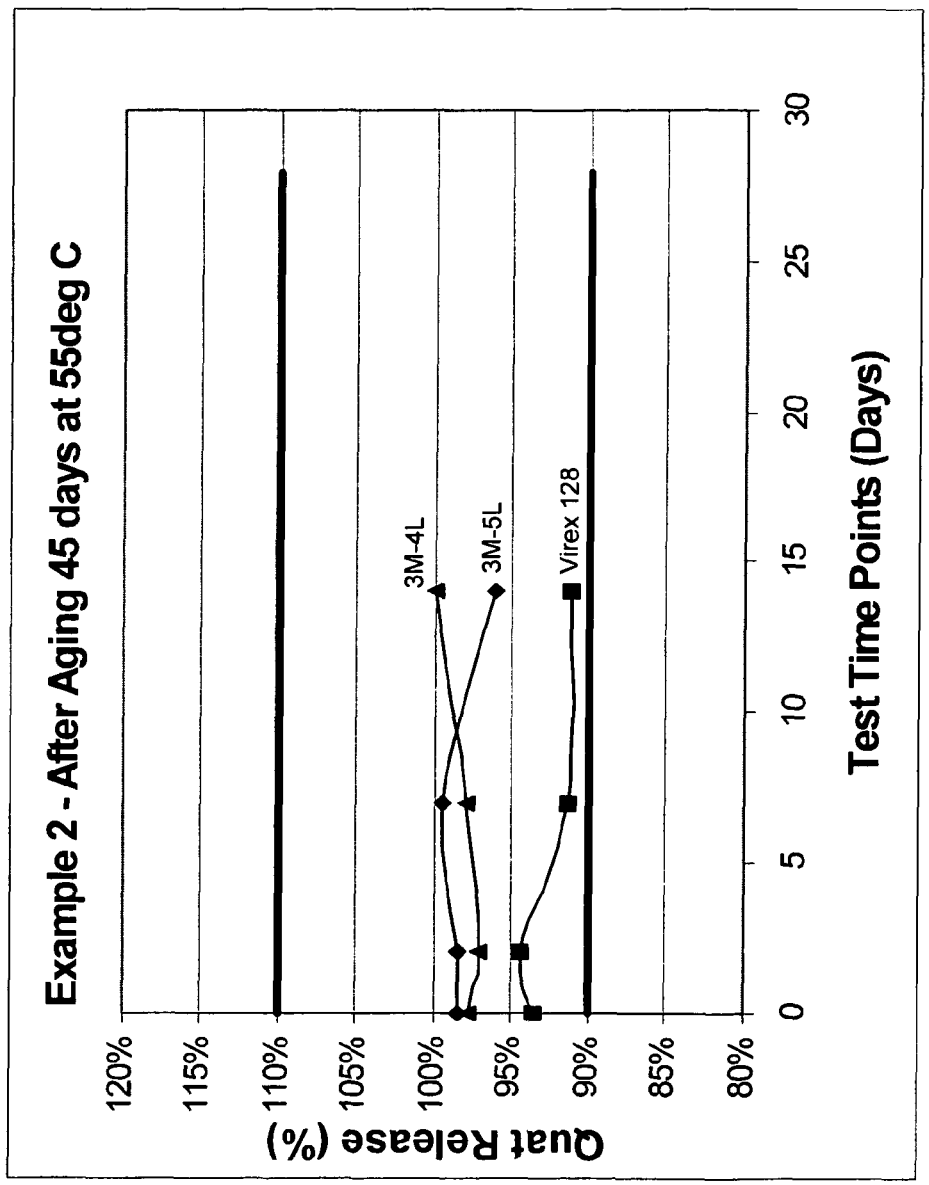
FIG. 11 is a plot of the percentage active disinfectant in the expressed solution, at various testing time periods, from a wiper of the present invention aged for 45 days at 55 degrees C. for different disinfectant solutions.

As can be seen in the progression from FIG. 9 to FIG. 11, the quat release decreased with longer periods of heated-aging. However, the wipers were able to stay within the desired range of 90 to 110 percent quat release in each case.

Additionally, as can be seen from FIGS. 9, 10, and 11, the quat release remained fairly steady (i.e., low variability) throughout the quat release testing period.

It will be appreciated that the foregoing examples and discussion, given for purposes of illustration, are not to be construed as limiting the scope of this invention, which is defined by the following claims and all equivalents thereto.

We claim:

1. A dry wiper which is stable in a disinfectant solution comprising;
    a dry substrate comprising synthetic fibers; and
    a disinfectant release treatment comprising lauryldimethylammoniumhydroxypropyl alkyl polyglucoside present on the substrate and the release treatment is present at an add-on level of about 0.20 percent or less, based on the weight of the substrate;
    wherein the disinfectant release treatment renders the wiper disinfectant stable for both quaternary ammonium disinfectant solutions and bleach disinfectant solutions such that when the wiper is saturated with a quaternary ammonium disinfectant solution or a bleach disinfectant solution and the wiper is capable of expressing between 90% and 110% of an active disinfectant saturating the wiper to a substrate being wiped with the wiper.

* * * * *